(12) United States Patent
Pacetti et al.

(10) Patent No.: US 8,546,412 B2
(45) Date of Patent: Oct. 1, 2013

(54) METHODS OF TREATING HEART FAILURE

(75) Inventors: Stephen Dirk Pacetti, San Jose, CA (US); Jeffrey B. Huff, Lincolnshire, IL (US); Paul Macke Consigny, San Jose, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/332,509

(22) Filed: Dec. 21, 2011

(65) Prior Publication Data

US 2013/0165461 A1 Jun. 27, 2013

(51) Int. Cl.
*A01N 43/54* (2006.01)
*A61K 31/505* (2006.01)

(52) U.S. Cl.
USPC ............................................ 514/275; 514/256

(58) Field of Classification Search
USPC .................................. 514/256, 275
See application file for complete search history.

(56) References Cited

U.S. PATENT DOCUMENTS

| 5,797,870 | A | * | 8/1998 | March et al. ................ 604/506 |
|---|---|---|---|---|
| 6,086,582 | A | * | 7/2000 | Altman et al. ................ 606/41 |
| 7,262,318 | B2 | * | 8/2007 | Hamanaka et al. ............ 560/17 |
| 7,320,675 | B2 | * | 1/2008 | Pastore et al. ................ 604/67 |
| 2006/0240070 | A1 | * | 10/2006 | Cromack et al. ............ 424/426 |
| 2008/0269105 | A1 | * | 10/2008 | Taft et al. ............ 514/2 |
| 2009/0216317 | A1 | * | 8/2009 | Cromack et al. ............ 623/1.42 |
| 2010/0210792 | A1 | * | 8/2010 | Taft et al. .................... 525/411 |

OTHER PUBLICATIONS

Altman et al., "Exploring heart lymphatics in local drug delivery", 2003, Lymphat Res Biol., vol. 1(1), pp. 47-54.*
Scott et al., "Aiming for the heart: targeted delivery of drugs to diseased cardiac tissue", Apr. 2008, Expert Opin Drug Deliv.; vol. 5(4):459-70.*

* cited by examiner

*Primary Examiner* — My-Chau T Tran
(74) *Attorney, Agent, or Firm* — Lisa A. Chiarini; Walter M. Egbert, III; Hughes Hubbard & Reed LLP

(57) ABSTRACT

Methods of treating heart failure by administration of beneficial agents to the heart.

23 Claims, No Drawings

METHODS OF TREATING HEART FAILURE

TECHNICAL FIELD

The subject matter relates to treating and/or inhibiting heart failure.

BACKGROUND

Heart failure, often referred to as congestive heart failure ("CHF") is a major health problem in the United States, affecting about 2% of adults, and about 6 to 10% of adults over the age of sixty-five. The magnitude of heart failure as a clinical problem has emphasized the need to develop new treatment strategies.

Heart failure is a debilitating disease that is generally defined as the inability of the heart to supply sufficient blood flow to the tissues and organs of the body. In some instances, the cardiac output is low, the body becomes congested with fluid. However, fluid overload is not co-terminus with heart failure and some patients may be euvolaemic or dehydrated. The effects of CHF cause the heart muscle to work harder. Over time, increases in workload will produce changes to the heart muscle. In particular, the heart may suffer from reduced force of contraction due to overloading ventricle. Typically, increased filling of the ventricle results in an increased force of contraction and a rise in cardiac output. During heart failure, the ventricle fills with blood but the heart muscle has a reduced ability to cross link actin and myosin fibers over the stretched heart muscle, and consequently, the heart muscle contraction becomes less efficient. Reduced contractility of the heart can cause also reduce stroke volume. Other changes in the heart itself include: loss of one's cardiac reserve, especially during exercise, increased heart rate, which may be stimulated by increased sympathetic activity to maintain cardiac output, arrhythmias, hypertropy (an increase in physical size) of the myocardium, enlargement of the ventricles, contributing to the enlargement and spherical shape of the failing heart. The increase in ventricular volume also causes a reduction in stroke volume due to mechanical and contractile inefficiency.

In chronic heart failure, the reduced cardiac output can cause various changes in the rest of the body, such as decreased arterial blood pressure, increased sympathetic stimulation, which may cause increased secretion of vasopressin, fluid retention and consequently increased blood pressure. Other changes include reduced perfusion to organs such as the kidneys, which may cause secretion of renin, an enzyme that catalyses the production of the vasopressor angiotensin. Angiotensin and its metabolites can cause further vasocontriction, and stimulate increased secretion of aldosterone, which can further promote salt and fluid retention at the kidneys, also increasing the blood volume and blood pressure.

Chronic high levels of hormones such as renin, angiotensin, and aldosterone can negatively affect the myocardium, causing structural remodeling of the heart over the long term. Thus, the maladies of chronic heart failure can be persistent and pervasive.

The National Health and Nutrition Examination Survey (NHANES I) identified the following causes of heart failure: ischemic heart disease, hypertension, valvular heart disease, dilated cardiomyopathy, obesity, and diabetes. The current standards of treatment for heart failure is typically centered on medical treatment using angiotensin-converting enzyme (ACE) inhibitors, diuretics, beta-blockade, and digitalis. Cardiac resynchronization therapy (CRT) may also be employed, if a bi-ventricular pacing device is implanted. New treatments are needed to manage heart failure.

SUMMARY

To achieve these, and other advantages, and in accordance with the purpose of the disclosed subject matter, as embodied and broadly described, one aspect of the disclosed subject matter is directed to treating heart failure in a subject. The method includes administering a prodrug directly to the heart muscle. In this regard, the prodrug can be delivered to the pericardium, myocardium or other tissue of the heart. The prodrug can then be converted in situ to an active drug for treating heart failure, including acute and chronic heart failure.

In another aspect of the disclosed subject matter, a method of reducing heart failure after myocardial infarction is provided. In this regard, the method includes obtaining platelets from a donor and increasing the stromal cell derived factor (SDF-1) content of the donor platelets. The donor platelets with increased SDF-1 are administered, directly or indirectly, to the heart of the subject. For example, the donor platelets can be administered to the myocardium or coronary artery by intravenous injection or local delivery though a lumen.

The administered donor platelets can bind to the surfaces of an injured artery within the infarct zone. Alternatively, the administered donor platelets may aggregate to form microvascular obstructions in the infarct zone. In either of the above cases, the net result is increased platelet deposition and thereby increased SDF-1 delivery by these loaded platelets to the injury site. Further, the SDF-1 delivered by the donor platelets can stimulate the recruitment and sequestration of progenitor cells and replace myocardial cells and promote revascularization of the infarct site, thereby promoting healing and myocardial wall thickening and inhibiting cardiac wall expansion that leads to heart failure.

The SDF-1 content can be increased by electroporating the donor platelets in the presence of SDF-1. If desired, the platelets can be activated with a cytokine, such as thrombopoietin prior to administration.

DETAILED DESCRIPTION OF EXEMPLARY EMBODIMENTS

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Overview

The exemplary embodiments relate to the treatment of heart failure. Heart failure, as used herein, is defined as an inability of the heart to supply sufficient blood flow to meet the needs of the body. In some embodiments, the treatment includes locally administering a prodrug to the heart muscle, for example via the pericardium. The prodrug converts to an active drug in situ. The term "prodrug" as used herein means a precursor of a drug that undergoes a chemical conversion before becoming an active pharmacological agent. The term "active drug" as used herein means an active pharmacological agent. In some embodiments, the treatment includes administering platelets having increased content of Stromal Derived Factor 1.

Treatments of Heart Failure

In one aspect, a method for treating heart failure in a subject is provided. As used herein a "subject" is an individual in need of said treatment. The method includes administering a prodrug to the heart of the subject; and converting or causing conversion of the prodrug to an active drug in situ at the heart. In this regard, the outcome can be prevented and effectiveness improved by the local delivery of drug to the heart.

In one embodiment, the prodrug is lipophilic. The lipophilic prodrug is advantageous due to the typically high lipid content of the pericardium. The fatty deposit region of the pericardium presents an ideal environment to deliver and concentrate a lipophilic prodrug. Being more lipophilic, the prodrug will have a longer residence time in the fatty tissue of the pericardium than the parent drug. One measure of lipophilicity is the n-octanol/water partition coefficient. Preferably, the lipophilic prodrug has an octanol/water partition coefficient at least twice as large as that of the parent drug. After local delivery, the lipophilic prodrug is available for enzymatic conversion or other catalyzed conversion to an active form of the drug in the vicinity of the heart muscle.

Several classes of drugs offer potential benefit when administered locally for congestive heart failure. One such class are the statins. Rosuvastatin and a hydrophobic prodrug lauryl alcohol derivative of rosuvastatin have the following structures:

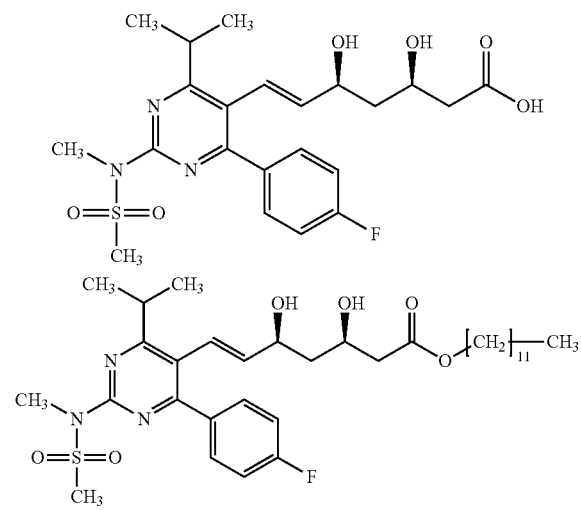

In vivo, the lauryl alcohol ester would slowly hydrolyze generating the parent drug. In another embodiment, the angiotensin converting enzyme (ACE) inhibitor Captopril is converted to a lauric acid thioester prodrug derivative with greater lipophilicity than Captopril.

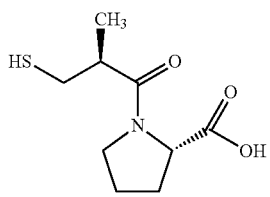

-continued

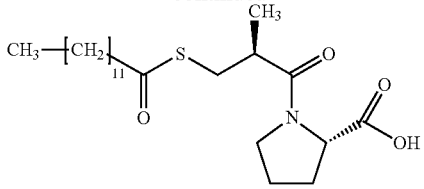

In vivo, the thioester will hydrolyze more rapidly than an aliphatic ester, liberating the parent drug molecule. In one embodiment, lipophilic groups can be attached to an active drug molecule, such as but not limited to alkyl chains, polyethers, branched hydrocarbons, or other suitable chemical moieties. The attachments of lipophilic groups preferably include various reversible attachment moieties such as esters, amides, peptides, disulfides, thioesters, ketals, acetals, orthoesters, N-hydroxyy succinimidyl or other linkers that are subject to nucleophilic attack, hydrolysis, reduction, oxidation, or other enzyme or naturally catalyzed reactions to release the active drug moiety from the lipophilic region of the heart and induce distribution within the target tissue for a therapeutic effect.

In one embodiment, the prodrug is administered to the pericardial sac of the heart. The drug may be introduced into the pericardial sac via a subxyphoid injection. An alternate technique is via a needle injection catheter introduced through the venous system into the right atrium, and then a transatrial wall needle injection into the pericardial sac. In another embodiment, the prodrug is administered directly to the myocardium.

In another aspect, the bioavailability of an active drug for treating heart failure is increased by the local delivery of a prodrug that is converted to an active drug in situ at in particular can be increased at the site of treatment. In this regard, the toxicity of systemic delivery of active agents can be avoided. Thus, toxicity associated with the active drug is reduced as compared to systemic delivery of the active drug. There are several examples of local delivery of a therapeutic agent in order to avoid systemic effects. One such example is the Gliadel wafer used to treat malignant glioma. This releases carmustine locally, avoiding the higher dose needed if it were administrated systemically and the toxicity of systemic administration. A second example would be the drug eluting stent (DES) used to treat obstructive coronary artery disease. For example, the XIENCE® V drug eluting stent releases everolimus locally to prevent neointimal hyperplasia after stent which leads to restenosis. Research has been performed in using systemic administration of drugs such as sirolimus or everolimus in combination with metallic stents. Sufficiently high oral doses of these drugs can reduce restenosis. However, common side effects are nausea, abdominal pain, and bacterial infections.

In another aspect, a method of treating or inhibiting heart failure is provided after an ischemic event, such as myocardial infarction. In this regard, platelets are obtained from a donor and the Stromal Derived Factor-1 (SDF-1) content is increased. In this regard, the injury site exposes platelet binding sits and releases platelet activators. A cascade effect including recruitment of SDF-1 loaded platelet occurs, which release SDF-1 locally at the site. SDF-1 is a progenitor cell chemoattractant, thus progenitor cells are also recruited to th injury site. Differentiation into myocardial and vascular cells plus cytokine and grown factor release enhance cell recruitment, proliferation, and matrix deposition; all of which promotes and improves healing of the injury including increasing cardiac wall thickening and contractility, and decreasing occurrences of heart failure.

In accordance with this aspect, modified donor platelets are administered to a subject. The SDF-1 content of the platelets is increased by electroporating the donor platelets in the presence of SDF-1. The Electroporation increases SDF-1 content and platelet activation increases surface expression. Other cells that may be recruited to the infarct site include neutrophils and macrophages. These cells can also be electroporated to increase SDF-1. SDF-1 protein can be obtained from various sources including platelets, smooth muscle cells, endothelial cells and macrophages.

The method includes administering the modified platelets to a coronary artery. For example, a coronary artery that supplies an infarcted myocardium. Alternatively, the platelets can be administered into the left ventricle (upstream of the coronary circulation) or by intra-arterial or intravenous injection.

In another embodiment, platelet surface expression of SDF-1 is increased by activation by thrombin or cytokine stimulation by a soluble kit ligand, or thrombopoietin. Surface bound SDF-1 can bind to CXCR4 receptors on circulating progenitor cells and facilitate cell recruitment. The recruitment of progenitor cells can increase cardiac mass and increase cardiac shortening.

In regard to the method, the modified platelets will bind to the surfaces of injured arteries within the infarct zone or will aggregate to form microvascular obstructions in the infarct zone. The platelet activation within the infarct zone will stimulate the expression of SDF-1 on the surface of the platelet or release into the extracellular fluid. The SDF-1 can stimulate the recruitment and sequestration of progenitor cells to replace myocardial cells and/or promote revascularization of the infarct site. Accordingly, the method described can result in improved myocardial function and reduce the likelihood of heart failure, in particular after an ischemic event such as myocardial infarction. Further, the mobility of stem cells to the heart can reduce the severity of the heart failure.

The above description provides several methods and materials of the invention. This invention is susceptible to modifications in the methods and materials, as well as alterations in the fabrication methods and equipment. Such modifications will become apparent to those skilled in the art from a consideration of this application or practice of the invention provided herein. Consequently, it is not intended that this invention be limited to the specific embodiments provided herein, but that it cover all modifications and alternatives coming within the true scope and spirit of the invention as embodied in the attached claims. Any patents, applications, and other references cited herein are hereby incorporated by reference in their entirety.

What is claimed is:

1. A method for treating heart failure in a subject, the method comprising:
    administering a prodrug to the heart of the subject; and
    converting the prodrug to an active drug in situ at the heart, wherein the prodrug is at least one of a fatty alcohol ester derivative of rosuvastatin, fatty alcohol ester derivative of a statin, fatty acid thioester derivative of captopril, or a fatty acid thioester derivative of an ACE inhibitor, and
    wherein the active drug is at least one of rosuvastatin, simvastatin, atorvastatin, a statin, captopril, enalapril, lisinopril, and ACE inhibitor, spironolactone, or an aldosterone receptor inhibitor.

2. The method of claim 1, wherein the prodrug is lipophilic.

3. The method of claim 1, wherein the prodrug is administered to the pericardial sac of the heart.

4. The method of claim 1, wherein the prodrug is administered to the myocardium.

5. The method of claim 1, wherein the prodrug is converted to an active drug by one or more enzymes.

6. The method of claim 1, wherein the prodrug has an octanol/water partition coefficient at least double that of its parent drug compound.

7. The method of claim 1, wherein the prodrug is converted to an active drug by hydrolysis, oxidation, or reduction.

8. The method of claim 1, wherein bioavailability of the active drug is increased.

9. The method of claim 1, wherein bioavailability of the active drug is increased at the site of treatment.

10. The method of claim 1, wherein the heart failure is chronic.

11. The method of claim 1, wherein toxicity associated with the active drug is reduced as compared to systemic delivery of the active drug.

12. The method of claim 1, wherein the prodrug is administered via subxyphoid injection.

13. The method of claim 1, wherein the prodrug is administered via a drug eluting stent.

14. A method for treating heart failure in a subject, the method comprising:
    administering an inactive form of a lipophilic drug into a fatty tissue of the heart of a subject.

15. The method of claim 14, wherein the inactive form of the lipophilic drug is capable of converting to an active form.

16. The method of claim 15, wherein the inactive form of the drug is converted to the active form by enzymatic activity in situ at the heart tissue.

17. The method of claim 15, wherein the inactive form of the drug is converted to the active form by hydrolysis, oxidation or reduction reactions in situ at the heart tissue.

18. The method of claim 14, wherein the inactive form of the drug is a prodrug.

19. The method of claim 14, wherein the heart failure is chronic.

20. The method of claim 14, wherein the heart failure is acute.

21. The method of claim 14, wherein the inactive form of the drug has an octanol/water partition coefficient at least double that of its parent drug.

22. The method of claim 14, wherein the administering step includes subxyphoid injection.

23. The method of claim 14, wherein the administering step includes administration from a stent.

* * * * *